US012752003B2

(12) United States Patent
Chen et al.

(10) Patent No.: US 12,752,003 B2
(45) Date of Patent: Oct. 6, 2026

(54) LIPIDATED FLIPr AND USES THEREOF IN VACCINE

(71) Applicant: National Health Research Institutes, Miaoli County (TW)

(72) Inventors: Hsin-Wei Chen, Miaoli County (TW); Ming-Shu Hsieh, Miaoli County (TW); Shih-Jen Liu, Miaoli County (TW); Ching-Len Liao, Miaoli County (TW)

(73) Assignee: NATIONAL HEALTH RESEARCH INSTITUTES, Miaoli County (TW)

( * ) Notice: Subject to any disclaimer, the term of this patent is extended or adjusted under 35 U.S.C. 154(b) by 479 days.

(21) Appl. No.: 18/229,010

(22) Filed: Aug. 1, 2023

(65) Prior Publication Data

US 2024/0033350 A1 Feb. 1, 2024

Related U.S. Application Data

(60) Provisional application No. 63/394,132, filed on Aug. 1, 2022.

(51) Int. Cl.
*A61K 39/00* (2006.01)
*A61K 39/09* (2006.01)
(Continued)

(52) U.S. Cl.
CPC ............ *A61K 39/39* (2013.01); *A61K 39/092* (2013.01); *A61K 39/12* (2013.01); *A61K 39/145* (2013.01); *A61K 39/215* (2013.01); *A61P 31/04* (2018.01); *A61P 31/14* (2018.01); *A61P 31/16* (2018.01); *A61K 2039/5252* (2013.01); *A61K 2039/55516* (2013.01); *A61K 2039/575* (2013.01)

(58) Field of Classification Search
CPC ...... A61K 39/39; A61K 39/092; A61K 39/12; A61K 39/145; A61K 39/215; A61K 2039/5252; A61K 2039/55516; A61K 2039/575; A61K 2039/57; A61K 39/085; A61P 31/04; A61P 31/14; A61P 31/16; A61P 37/04; C12N 2770/20034; C12N 2770/24134; C12N 2760/16134; C12N 2770/24034; Y02A 50/30
See application file for complete search history.

(56) References Cited

FOREIGN PATENT DOCUMENTS

WO WO2018128931 * 7/2018 ............. A61K 48/00

OTHER PUBLICATIONS

Kim, I. J. et al. Efficacy of an inactivated Zika vaccine against virus infection during pregnancy in mice and marmosets. NPJ vaccines, 7(1), 9. (Year: 2022).*

(Continued)

*Primary Examiner* — M Franco G Salvoza
*Assistant Examiner* — Claire Cornelius
(74) *Attorney, Agent, or Firm* — MUNCY, GEISSLER, OLDS & LOWE, P.C.

(57) ABSTRACT

The present disclosure relates to a vaccine composition, comprising a recombinant lipidated FLIPr (rLF), and the use thereof in enhancing humoral and cellular immune responses. The recombinant lipidated FLIPr of present invention may be used as a vaccine candidate that can induce anti-FLIPr responses to overcome FLIPr-mediated inhibition. And unexpectedly, the recombinant lipidated FLIPr may be used as an adjuvant that can enhance other vaccine immune responses, especially in subunit vaccines and inactivated virus vaccines.

11 Claims, 15 Drawing Sheets

(51) Int. Cl.

| | |
|---|---|
| ***A61K 39/12*** | (2006.01) |
| ***A61K 39/145*** | (2006.01) |
| ***A61K 39/215*** | (2006.01) |
| ***A61K 39/39*** | (2006.01) |
| ***A61P 31/04*** | (2006.01) |
| ***A61P 31/14*** | (2006.01) |
| ***A61P 31/16*** | (2006.01) |

(56) References Cited

OTHER PUBLICATIONS

Kuo, T. Y. et al. Development of CpG-adjuvanted stable prefusion SARS-COV-2 spike antigen as a subunit vaccine against COVID-19. Scientific reports, 10(1), 20085. (Year: 2020).*

Pulendran, B.S. et al. Emerging concepts in the science of vaccine adjuvants. Nature reviews. Drug discovery, 20(6), 454-475. (Year: 2021).*

Wiedinger, K. et al. Isotype-specific outcomes in Fc gamma receptor targeting of PspA using fusion proteins as a vaccination strategy against *Streptococcus pneumoniae* infection. Vaccine, 38(35), 5634-5646. (Year: 2020).*

Chen, H. et al. A novel technology for the production of a heterologous lipoprotein immunogen in high yield has implications for the field of vaccine design. Vaccine, 27(9), 1400-1409. (Year: 2009).*

* cited by examiner

LIPIDATED FLIPr AND USES THEREOF IN VACCINE

CROSS REFERENCE TO RELATED APPLICATIONS

This application claims priority of U.S. Provisional Application No. 63/394,132 filed on Aug. 1, 2022 under 35 U.S.C. § 119(e), the entire contents of all of which are hereby incorporated by reference.

FIELD OF THE DISCLOSURE

The present disclosure relates to a field of vaccine preparation; more particularly, to a lipidated FLIPr (rLF) and uses thereof in vaccine as a vaccine candidate and an adjuvant.

BACKGROUND OF THE DISCLOSURE

*Staphylococcus aureus* can be a harmless microorganism. It becomes an invasive pathogen when *S. aureus* enters the germ-free regions of the host once epithelial barriers or immune systems turn out to be compromised (Clin Microbiol Rev 2015. 28: 603-661; Lancet Infect Dis 2005. 5: 751-762; Front. Microbiol. 2018. 9:2419). Nasal *S. aureus* carriage is the main reservoir for *Staphylococcus aureus*, which is one of key risk factors resulting the pathogenic process of hospital and community acquired infections (*N. Engl. J. Med.* 2001. 344:11-16; *Lancet* 2004. 364(9435): 703-705). *S. aureus* has evolved various approaches to escape the attack from the immune system. The approaches used by this bacterium include resistance to antimicrobial peptide, and inhibition of neutrophil recruitment, phagocytosis, killing by ROS and neutrophil (*Microbial Pathogenesis* 2019, 131:259-269). Thus, molecules on the surface of bacteria and products for immune evasion are potential targets for S. vaccine development (*BMC Microbiology* 2010, 10:173).

Formyl Peptide Receptor-like 1 Inhibitor (FLIPr) is one of the immune evasion proteins produced by *S. aureus* to evade immune system via binding to C1q subcomponents or C1q complex, or binding to various Fcγ receptor subclasses resulting in competitive block of IgG-ligand binding. These interaction can increase *Staphylococcus aureus* survival in whole human blood (*Sci Rep.* 2016, 6:27996.) and inhibit Fc γ receptor-mediated effector functions (*J Immunol* 2013. 191: 353-362). Additionally, FLIPr is detected in many infecting isolates during biofilm formation in vitro (*Med Microbiol Immunol* 2017, 206:11-22). Therefore, FLIPr is a potential vaccine candidate to induce immune response for reducing *S. aureus* virulence and biofilm formation. In this invention, a vaccine candidate to induce anti-FLIPr responses is developed to overcome FLIPr-mediated inhibition.

Inactivated virus and recombinant protein (subunit vaccines), which are noninfectious, have significant safety advantages over live or live-attenuated vaccines. However, it is known that inactivated virus and recombinant protein exhibit low immunogenicity. Thus, these two vaccine types are generally formulated with an adjuvant to induce powerful immune responses. Currently, there are rare mucosal adjuvants approved for use in human vaccines.

Accordingly, a recombinant lipidated FLIPr is prepared in the present invention, and proven to evaluate its immunogenicity. The recombinant lipidated FLIPr alone elicts potent anti-FLIPr antibody responses to overcome FLIPr-mediated inhibition of phagocytosis. Also, the recombinant lipidated FLIPr mixed with inactivated virus or recombinant protein can enhance mucosal and systemic immune response to inactivated virus or recombinant protein.

SUMMARY OF THE DISCLOSURE

In one aspect, the present disclosure provides a vaccine composition, comprising a recombinant lipidated FLIPr (rLF).

In one embodiment, the recombinant lipidated FLIPr (rLF) comprises a lipidating sequence and a polypeptide of FLIPr.

In some embodiments, the recombinant lipidated FLIPr (rLF) is used to induce anti-FLIPr responses. In some embodiments, the recombinant lipidated FLIPr (rLF) is used to prevent phagocytosis inhibition caused by *S. aureus* FLIPr protein.

In some embodiments, the vaccine composition further comprises an immunogen, wherein the recombinant lipidated FLIPr (rLF) is used to enhance a vaccine immune response of the immunogen. In one embodiment, the immunogen is a recombinant subunit protein of a virus. In one embodiment, the immunogen is an inactivated virus.

In one embodiment, the immunogen is a recombinant envelope protein domain III of Zika virus (rZE3). In one embodiment, the immunogen is a recombinant mixture of the *S. pneumoniae* pneumococcal proteins (rAAC). In one embodiment, the immunogen is a recombinant trimeric spike protein of SARS CoV-2 (rTS).

In one embodiment, the immunogen is an inactived Zika virus (IZV). In one embodiment, the immunogen is an inactive influenza virus.

In one aspect, the present disclosure provides a method for enhancing a vaccine immune response, comprising immunizing a subject with a vaccine comprising a recombinant lipidated FLIPr (rLF) as an adjuvant. In one embodiment, the vaccine immune response is an antigen-induced antibody response. In one embodiment, the antigen-induced antibody response is a systemic and/or mucosal antibody response. In one embodiment, the vaccine immune response is a T cell response.

In one embodiment, the vaccine comprises an antigen (or antigens) adjuvanted with the recombinant lipidated FLIPr (rLF).

In some embodiments, the vaccine is a subunit vaccine. In one embodiment, the vaccine comprises a recombinant envelope protein domain III of Zika virus (rZE3) adjuvanted with the recombinant lapidated FLIPr.

In one embodiment, the vaccine comprises one or more *S. pneumoniae* pneumococcal proteins (rAAC) adjuvanted with the recombinant lipidated FLIPr (rLF).

In one embodiment, the vaccine comprises a recombinant trimeric spike protein of SARS CoV-2 (rTS) adjuvanted with the recombinant lipidated FLIPr (rLF).

In some embodiments, the vaccine is an inactivated virus vaccine. In one embodiment, the vaccine comprises an inactived Zika virus (IZV) adjuvanted with recombinant lipidated FLIPr (rLF). In one embodiment, the vaccine comprises an inactive influenza virus adjuvanted with the recombinant lipidated FLIPr (rLF).

The present disclosure is described in detail in the following sections. Other characteristics, purposes and advantages of the present disclosure can be found in the detailed description and claims.

DETAILED DESCRIPTION OF THE DISCLOSURE

Figure 1:
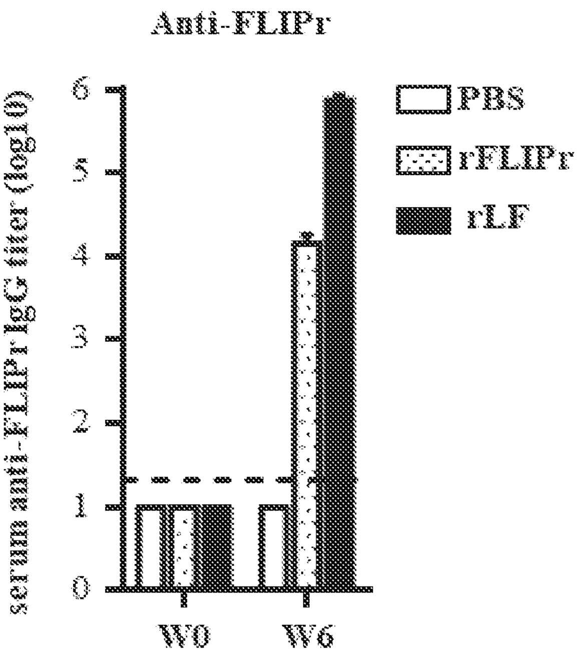
FIG. 1 shows the antibody responses induced by recombinant lipidated FLIPr (rLF). (A) The titers of anti-rFLIPr IgG antibodies in the serum before immunization (W0) or 6 weeks after immunization (W6) were determined by ELISA.

The present disclosure can be more readily understood by reference to the following detailed description of various embodiments of the disclosure, the examples, and the chemical drawings and tables with their relevant descriptions. It is to be understood that unless otherwise specifically indicated by the claims, the disclosure is not limited to specific preparation methods, carriers or formulations, or to particular modes of formulating the extract of the disclosure into products or compositions intended for topical, oral or parenteral administration, because as one of ordinary skill in the relevant arts is well aware, such things can, of course, vary. It is also to be understood that the terminology used herein is for the purpose of describing particular embodiments only and is not intended to be limiting.

As utilized in accordance with the present disclosure, the following terms, unless otherwise indicated, shall be understood to have the following meaning:

Often, ranges are expressed herein as from "about" one particular value and/or to "about" another particular value. When such a range is expressed, an embodiment includes the range from the one particular value and/or to the other particular value. Similarly, when values are expressed as approximations, by use of the word "about," it will be understood that the particular value forms another embodiment. It will be further understood that the endpoints of each of the ranges are significant both in relation to and independently of the other endpoint.

It must be noted that, as used in the specification and the appended claims, the singular forms "a," "an" and "the" include plural referents unless the context clearly dictates otherwise. Thus, unless otherwise required by context, singular terms shall include the plural and plural terms shall include the singular.

As used herein, the term "or" in the claims is used to mean "and/or" unless explicitly indicated to refer to alternatives only or the alternatives are mutually exclusive.

As used herein, the term "lipidated FLIPr (rLF)" refers to a polypeptide of FLIPr fused with a lipidating sequence at its N-terminus. The term "lipidating sequence" used herein refers to a non-naturally occurring amino acid sequence that facilitates lipidation in *E. coli* of a polypeptide carrying the lipidating sequence at its N-terminus.

The following examples are provided to aid those skilled in the art in practicing the present disclosure.

EXAMPLES

Example 1. Preparation of Recombinant Lipidated FLIPr (rLF)

To express the recombinant lipidated FLIPr (rLF), the *E. coli* C43(DE3) strain is transformed with plasmid pLF. The transformed cells are cultured with LB broth at 37-C overnight. The overnight culture is scaled up 50 times of the original volume in a 2 L-shake flask and incubated at 37° C. until the $OD_{600}$ reach to 0.6. Protein expression is induced ($OD_{600}$=0.6) by adding 1 mM IPTG, followed by incubation at 20° C. for 24 h. rLF is purified by disrupting the harvested cells in a French press (Constant Systems, Daventry, UK) at 27 Kpsi in homogenization buffer [20 mM Tris (pH 8.0), 40 mM sucrose, 400 mM NaCl and 10% glycerol]. The cell lysate is clarified by centrifugation with 32,000 rpm for 40 min in 4° C. Most of the rLF is present in inclusion bodies.

rLF is then solubilized with extraction buffer [10 mM $Na_2HPO_4$ (pH9.0) and 1% TritonX-100]. The extracted fraction is loaded onto immobilized metal affinity chromatography (IMAC) columns (BIO-RAD, Hercules, CA, USA, 2.5 cm i.d.×10.0 cm) containing 20 ml Ni-NTA resin (Qiagen, San Diego, CA, USA) to purify rLF. The column washed with the extraction buffer and the same buffer containing 20 mM imidazole. Then, rLF is eluted with the homogenization buffer containing 500 mM imidazole. The eluted rLF is dialyzed to 20 mM Tris (pH 8.0) three times for at least 6 h each time. After dialysis, the rLF is loaded onto a 20-ml Q Sepharose fast flow column (GE Healthcare, Little Chalfont, Buckinghamshire, UK). The column washed with dialysis buffer containing 200 mM NaCl, and then washed with a 100-fold column volume of dialysis buffer containing 0.1% Triton X-114 to remove the lipopolysaccharide. Next, the column is washed without 0.1% Triton X-114 to remove the residual detergent and rLF is eluted with elution buffer [10 mM Na2HPO4 (pH9.0), 300 mM NaCl and 8M Urea]. The eluted rLF is dialyzed to 10 mM $Na_2HPO_4$ (pH9.0) three times for at least 6 h each time.

The endotoxin levels of the purified rLF are determined by the Limulus amebocyte lysate (LAL) assay (Associates of Cape Cod, Inc., Cape Cod, MA), and the resulting endotoxin levels are <30 EU/mg. After dialysis the rLF is lyophilized and stored at −20° C. The fractions from each step are analyzed by SDS-PAGE and immunoblotted with anti-FLIPr and anti-Histag antibodies.

Example 2. Lipidated FLIPr (rLF) is a Vaccine Candidate that can Induce Anti-FLIPr Responses Antibody Responses Induced by Recombinant Lipidated FLIPr (rLF)

In order to validate that the lipidated FLIPr is a vaccine candidate, groups of mice are intranasally immunized three times with PBS, rFLIPr or rLF. PBS-immunized mice are served as the control. The titers of anti-rFLIPr IgG antibodies in the serum before immunization (W0) or 6 weeks after immunization (W6) are determined by ELISA.

As showed in FIG. 1, the lipidated FLIPr can strongly induce production of anti-FLIPr antibodies.

Recombinant Lipidated FLIPr (rLF)-Immunized Serum Overcome the FLIPr-Mediated Inhibition of Phagocytosis by Human Neutrophils The serum from immunized mice collected at 6-weeks post-immunization are used to opsonize phagocytosis of fluorescent staphylococci by human neutrophils. The 30 μg/ml rFLIPr are used to inhibit the phagocytosis. Phagocytosis is determined as the percentage of cells with fluorescent bacteria, or the relative geometric mean fluorescence intensity of cells with fluorescent bacteria.

Figure 2A:
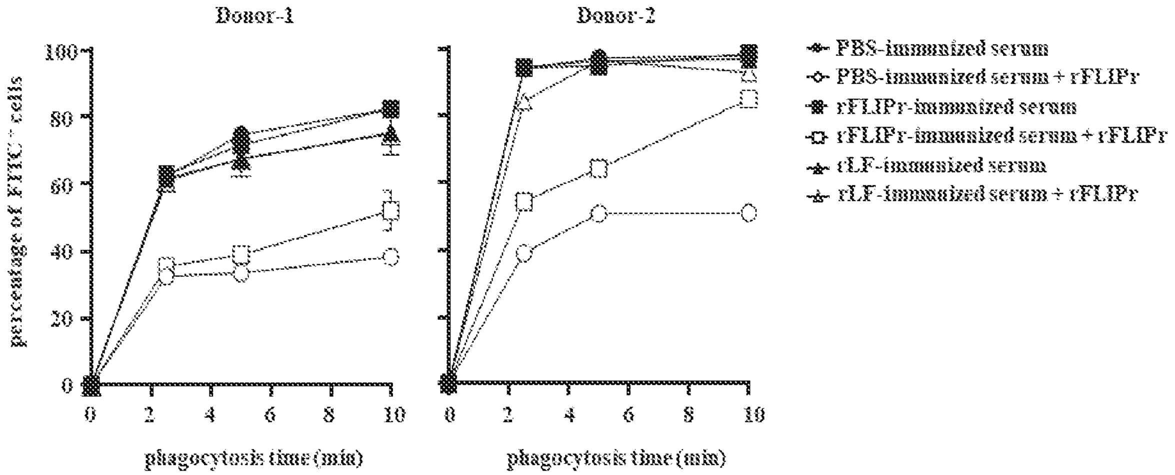
FIGS. 2A-2B show that the recombinant lipidated FLIPr (rLF)-immunized serum overcome the FLIPr-mediated inhibition of phagocytosis by human neutrophils. (A) The percentage of cells with fluorescent bacteria; (B) the relative geometric mean fluorescence intensity of cells with fluorescent bacteria.
Figure 2B:
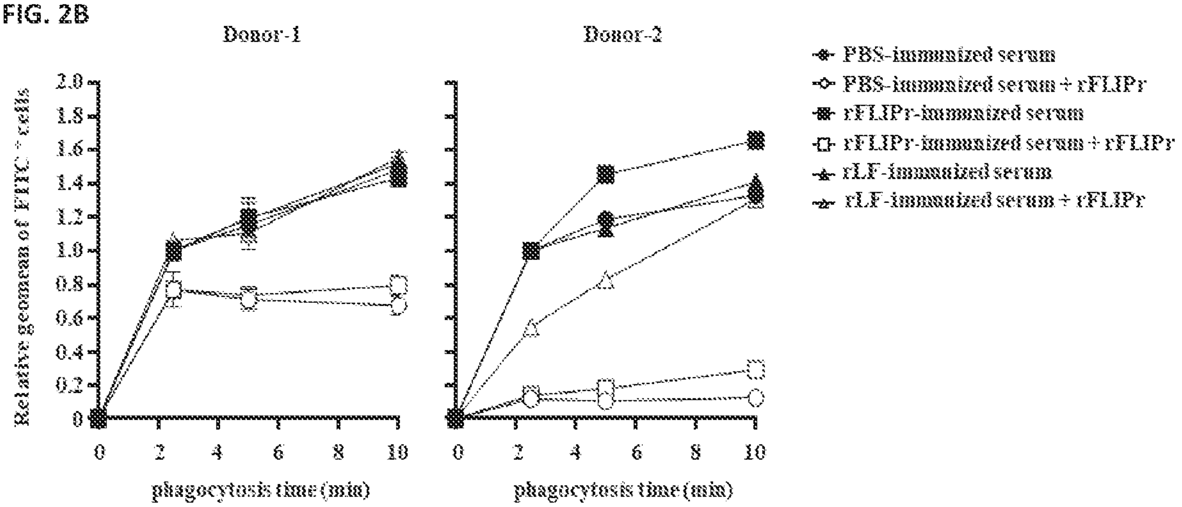

As showed in FIGS. 2A-2B, the lipidated FLIPr is a vaccine candidate that can induce anti-FLIPr responses to overcome FLIPr-mediated inhibition of phagocytosis by human neutrophils.

In summary, the lipidated FLIPr can be used as a vaccine to elicit antibodies against FLIPr, and also to prevent phagocytosis inhibition caused by *S. aureus* FLIPr protein.

Example 3. Lipidated FLIPr (rLF) is an Adjuvant that can Enhance Other Vaccine Immune Responses In this example, the role of the lipidated FLIPr in a vaccine as an adjuvant to enhance immune responses is identified by the immunizations of rLF with other immunogens, including recombinant proteins or inactivated vaccines.

Antibody Responses Induced by Recombinant Ovalbumin (rOVA) Adjuvanted with Recombinant Lipidated FLIPr (rLF).

Groups of mice intranasally immunized three times with PBS, rOVA or rOVA adjuvanted with rLF. PBS-immunized mice are served as the control. Serum samples are collected as indicated time after the first immunization. The titers of anti-rOVA IgG antibodies in the serum are determined by ELISA.

Figure 3:
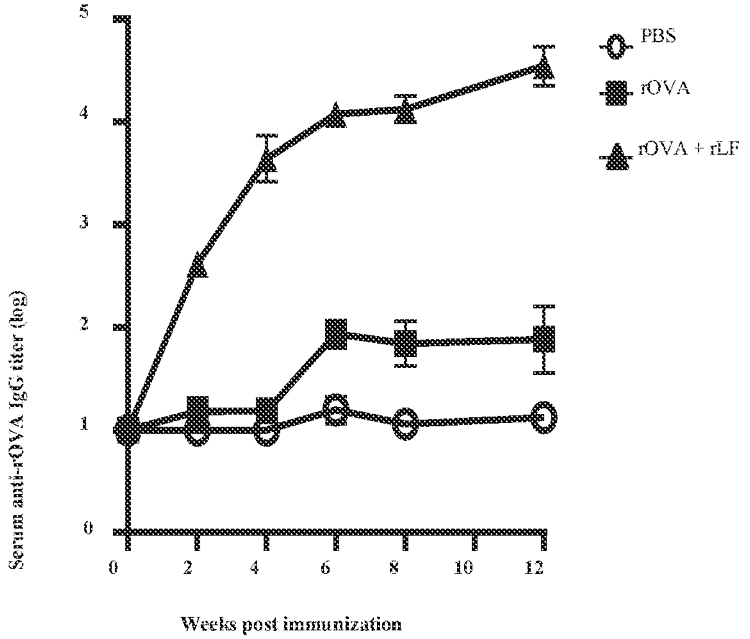
FIG. 3 shows the antibody responses induced by recombinant ovalbumin (rOVA) adjuvanted with recombinant lipidated FLIPr (rLF).
Figure 4A:
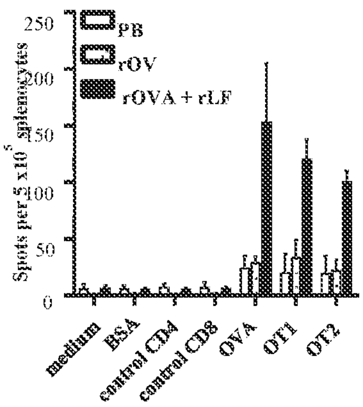
FIGS. 4A-4E show the T cell responses induced by rOVA adjuvanted with rLF. (A) Frequencies of IFN-γ producing cells were evaluated by ELISPOT. The supernatants were collected to evaluate levels of IFN-γ (B), IL-5 (C), IL-13(D), and IL-17A (E) by ELISA.
Figure 4B:
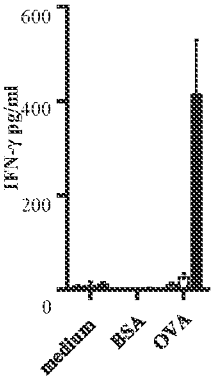
Figure 4C:
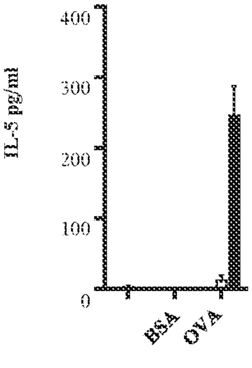
Figure 4D:
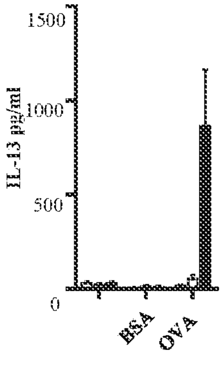
Figure 4E:
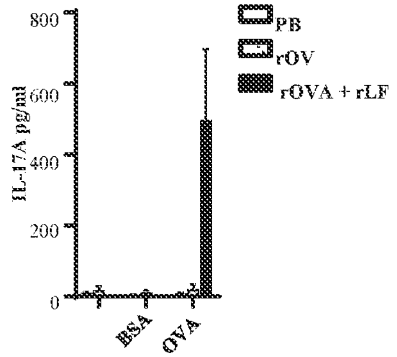

As showed in FIG. 3, the lipidated FLIPr strongly enhances rOVA-specific antibody.

T Cell Responses Induced by rOVA Adjuvanted with rLF

To further validate the functions of with rLF in the enhancement of T-cell immune responses, groups of mice intranasally immunized three times with PBS, rOVA or rOVA adjuvanted with rLF. PBS-immunized mice are served as the control. Splenocytes from immunized mice are cultured and stimulated with rOVA, OT-1 peptide, or OT-2 peptide for 2-3 days. Stimulation with BSA, control peptides, or medium alone served as controls. Frequencies of IFN-γ producing cells are evaluated by ELISPOT. The supernatants are collected to evaluate levels of IFN-γ, IL-5, IL-13, and IL-17A by ELISA.

As showed in FIGS. 4A-4E, the lipidated FLIPr-adjuvanted rOVA is able to stimulate OVA-specific CD4+ and $CD8^+$ as well as broad-spectrum T cell responses.

Antibody Responses Induced by Recombinant Envelope Protein Domain III of Zika Virus (rZE3) Adjuvanted with Recombinant Lipidated FLIPr (rLF)

Groups of mice intranasally immunized twice with PBS, rZE3 or rZE3 adjuvanted with rLF. PBS-immunized mice are served as the control. The titers of anti-rZE3 IgG and IgA antibodies in the serum are determined by ELISA. The Zika virus-neutralizing antibody titer of the serum samples is determined by FRNT.

Figure 5A:
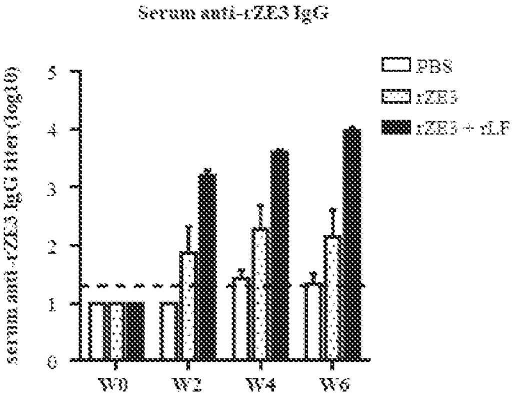
FIGS. 5A-5C show the antibody responses induced by recombinant envelope protein domain III of Zika virus (rZE3) adjuvanted with recombinant lipidated FLIPr (rLF). (A and B) The titers of anti-rZE3 IgG and IgA antibodies in the serum were determined by ELISA. (C) The Zika virus-neutralizing antibody titer of the serum samples was determined by FRNT.
Figure 5B:
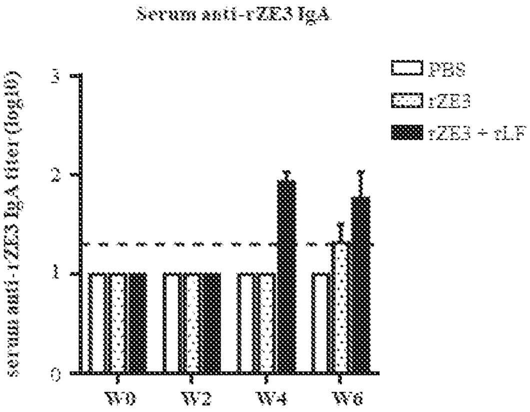
Figure 5C:
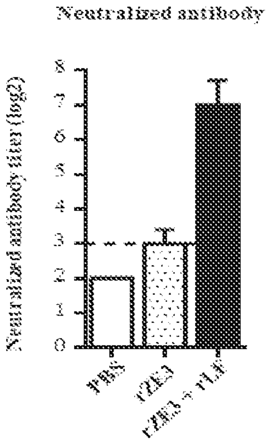

As showed in FIGS. 5A-5C, the lipidated FLIPr strongly enhances rZE3-induced antibody responses to against Zika virus.

Cytokine Production Profiles Induced by rZE3 Adjuvanted with rLF

Groups of mice are intranasally immunized twice with PBS, rZE3 or rZE3 adjuvanted with rLF (rZE3+rLF). PBS-immunized mice are served as the control. Splenocytes isolated from the immunized mice are cultured and stimulated with rZE3 for 4 days. Stimulation with BSA or medium alone served as controls. The supernatants are collected to evaluate levels of Th1-type cytokines (IFN-γ and IL-2), Th2-type cytokines (IL-5 and IL-13), and Th17-type cytokines (IL-17A) by ELISA.

Figure 6:
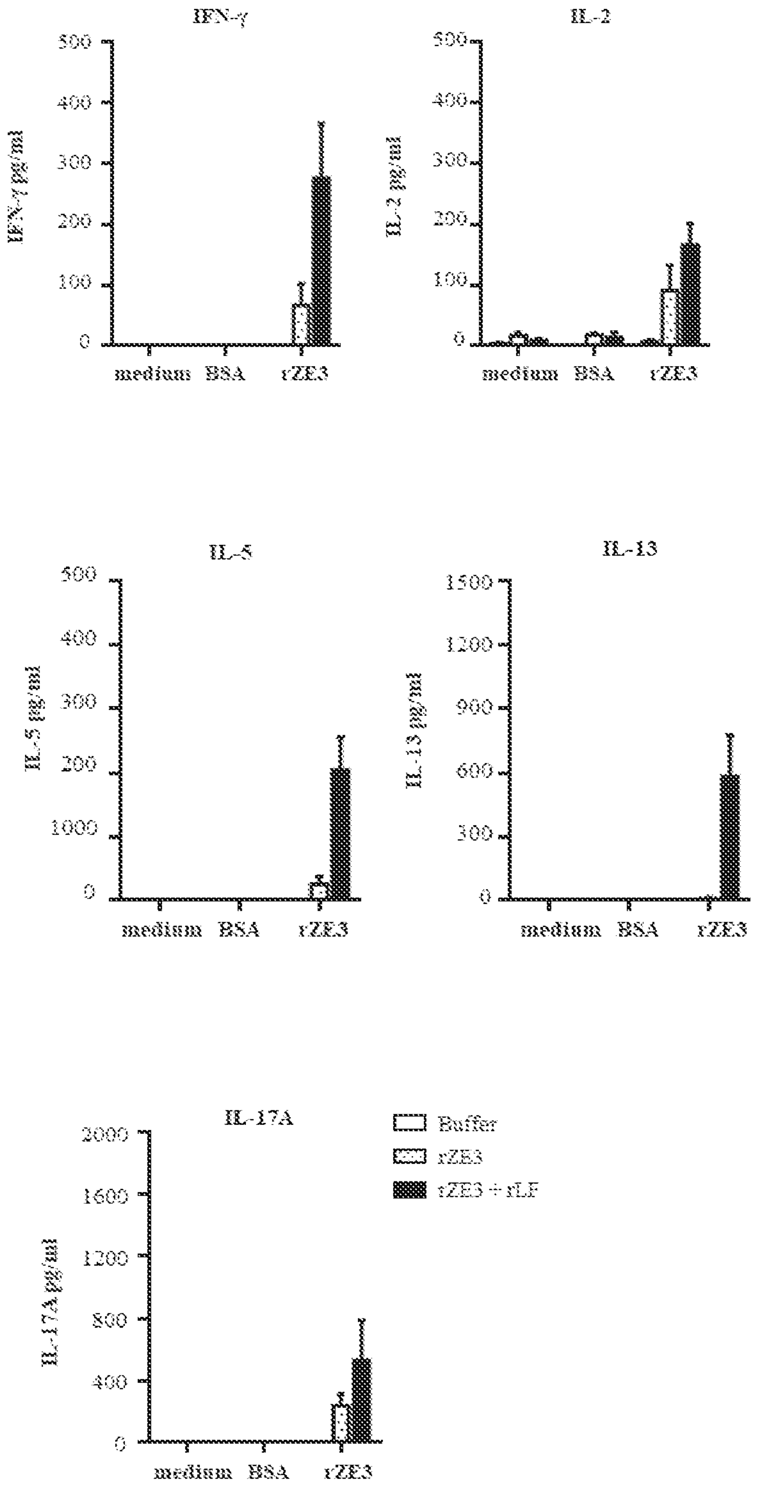
FIG. 6 shows the cytokine production profiles induced by rZE3 adjuvanted with rLF. The levels of Th1-type cytokines (IFN-γ and IL-2), Th2-type cytokines (IL-5 and IL-13), and Th17-type cytokines (IL-17A) were evaluated by ELISA.
Figure 7A:
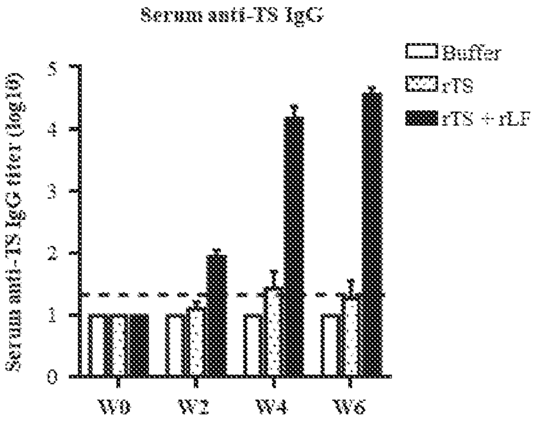
FIGS. 7A-7E show the antibody responses induced by intranasal immunization of recombinant trimeric spike protein of SARS CoV-2 (rTS) adjuvanted with recombinant lipidated FLIPr (rLF). (A and B) The titers of anti-rTS IgG and IgA antibodies in the serum were determined by ELISA. (C and D) The titers of anti-rTS IgA antibodies in mucosal tissue were determined by ELISA, including (C) nasal wash and (D) bronchoalveolar lavage fluid (BALF). (E) Vaccine-induced neutralizing antibody against SARS-CoV-2 was evaluated by neutralization assay.
Figure 7B:
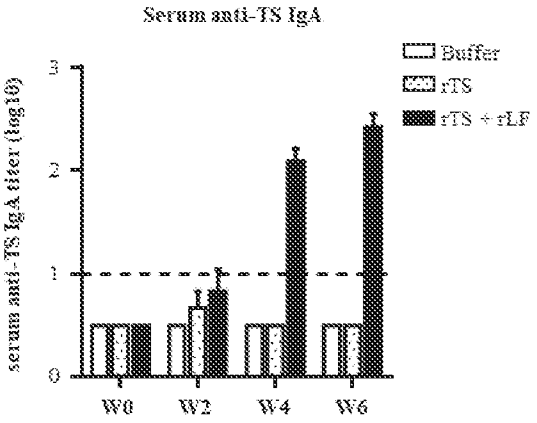
Figure 7C:
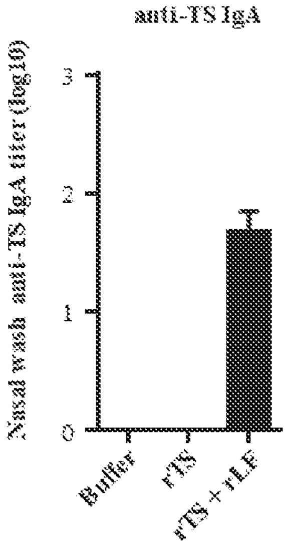
Figure 7D:
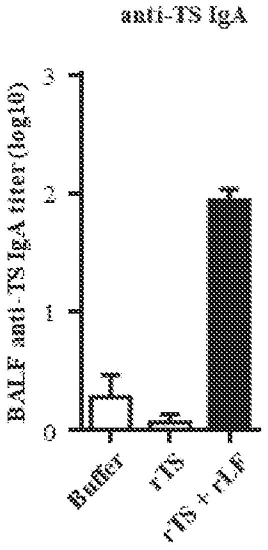
Figure 7E:
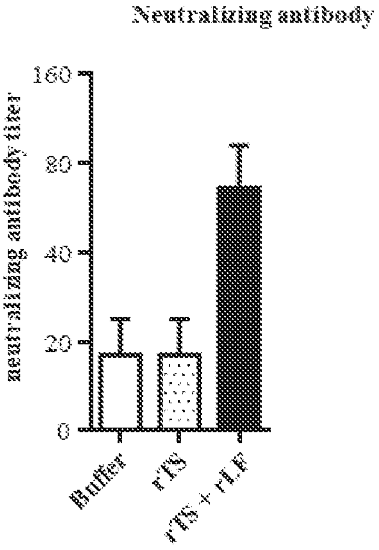

As showed in FIG. 6, the lipidated FLIPr-adjuvanted subunit vaccine of Zika virus is able to stimulate broad-spectrum T cell responses. The T cell responses in the rZE3+rLF treated mice are much higher than the rZE3 immunized mice.

Antibody Responses Induced by Intranasal Immunization of Recombinant Trimeric Spike Protein of SARS CoV-2 (rTS) Adjuvanted with Recombinant Lipidated FLIPr (rLF)

Groups of mice are vaccinated twice with PBS, rTS, or rTS adjuvanted with rLF (rTS+rLF). The titers of anti-rTS IgG and IgA antibodies in the serum are determined by ELISA. The titers of anti-rTS IgA antibodies in mucosal tissue are determined by ELISA, including nasal wash and bronchoalveolar lavage fluid (BALF). Vaccine-induced neutralizing antibody against SARS-CoV-2 is evaluated by neutralization assay.

As showed in FIGS. 7A-7E, the lipidated FLIPr strongly enhances rTS-induced systemic and mucosal antibody responses to against SARS-CoV-2.

Cytokine Production Profiles Induced by rTS Adjuvanted with rLF

Groups of mice are vaccinated twice with PBS, rTS, or rTS adjuvanted with rLF. PBS-immunized mice are alone served as control. Splenocytes are cultured and stimulated with rTS for 4 days. Stimulation with BSA or medium alone served as controls. The supernatants are collected to evaluate levels of the Th1-type cytokines (IFN-γ and IL-2), Th2-type cytokines (IL-5 and IL-13), and Th17-type cytokines (IL-17A) by ELISA.

Figure 8:
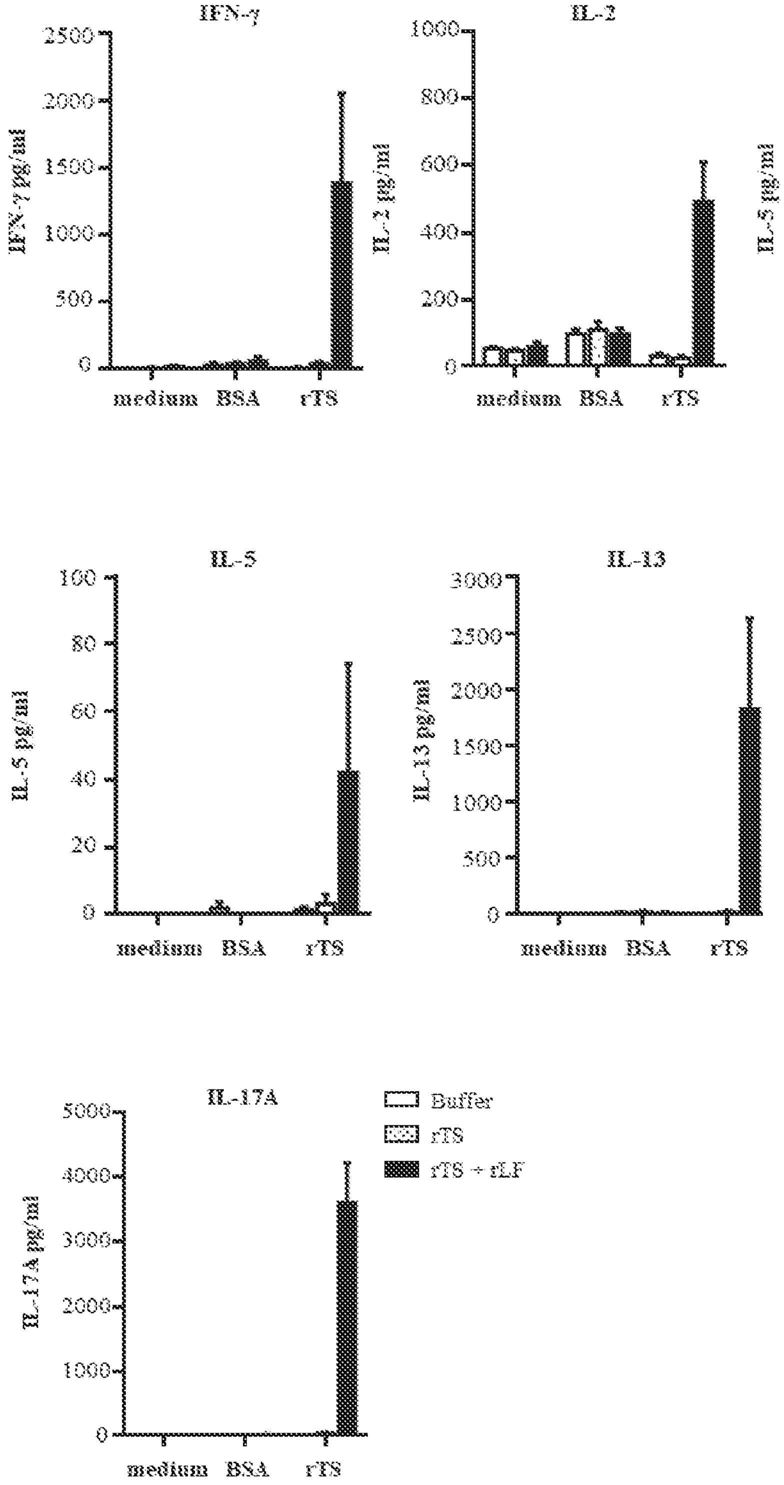
FIG. 8 shows the cytokine production profiles induced by rTS adjuvanted with rLF. The levels of Th1-type cytokines (IFN-γ and IL-2), Th2-type cytokines (IL-5 and IL-13), and Th17-type cytokines (IL-17A) were evaluated by ELISA.

As showed in FIG. 8, the lipidated FLIPr-adjuvanted subunit vaccine of SARS-CoV-2 spike protein (rTS+rLF) is able to stimulate broad-spectrum T cell responses. Additionally, the lipidated FLIPr effectively enhances SARS-CoV-2-specific T cell responses.

Systemic and Mucosal Antibody Responses Induced by Recombinant Mixture of the *S. pneumoniae* Pneumococcal Proteins (rAAC) Adjuvanted with Recombinant Lipidated FLIPr (rLF)

The mixture protein rAAC including pneumococcal surface adhesin A (rPsaA), pneumococcal surface protein A (rPspA), and pneumococcal surface protein C (rPspC). Groups of mice intranasally immunized three times with PBS, rAAC or rAAC adjuvanted with rLF (rAAC+rLF). The titers of anti-rPsaA, PspA, and PspC IgG in the serum are determined by ELISA.

Furthermore, the titers of anti-rPsaA, PspA, and PspC IgA in the nasal wash or BALF are determined by ELISA.

Figure 9:
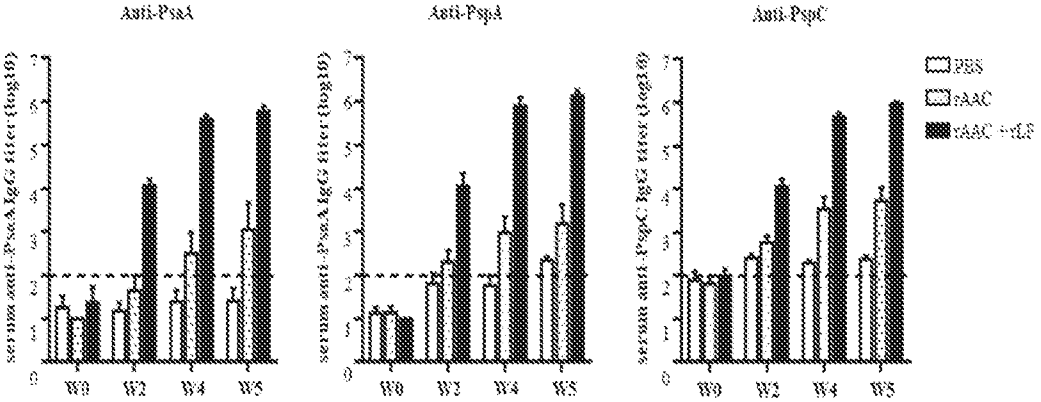
FIG. 9 shows the systemic antibody responses induced by recombinant mixture of the *S. pneumoniae* pneumococcal proteins (rAAC) adjuvanted with recombinant lipidated FLIPr (rLF).
Figure 10A:
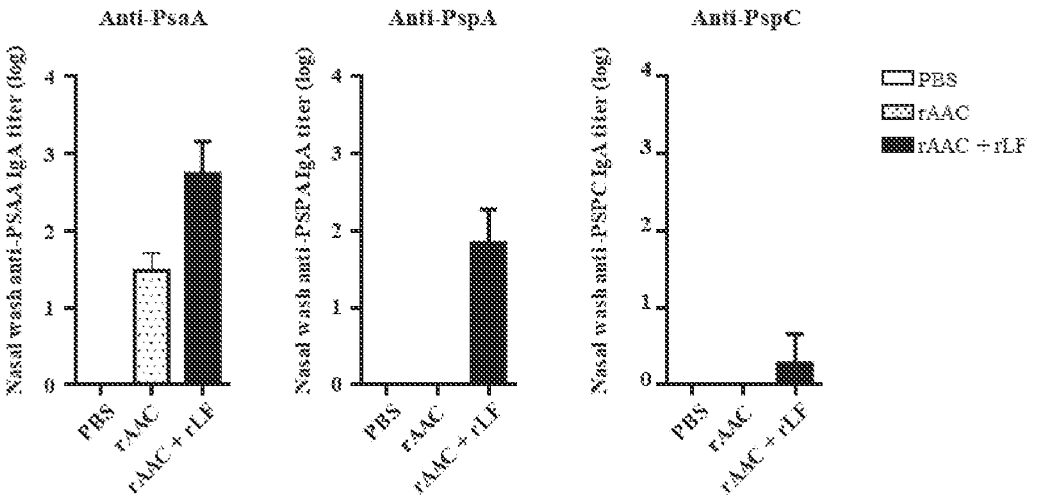
FIGS. 10A-10B show the mucosal antibody responses induced by rAAC adjuvanted with rLF. The titers of anti-rPsaA, PspA, and PspC IgA in the (A) nasal wash or (B) BALF were determined by ELISA.
Figure 10B:
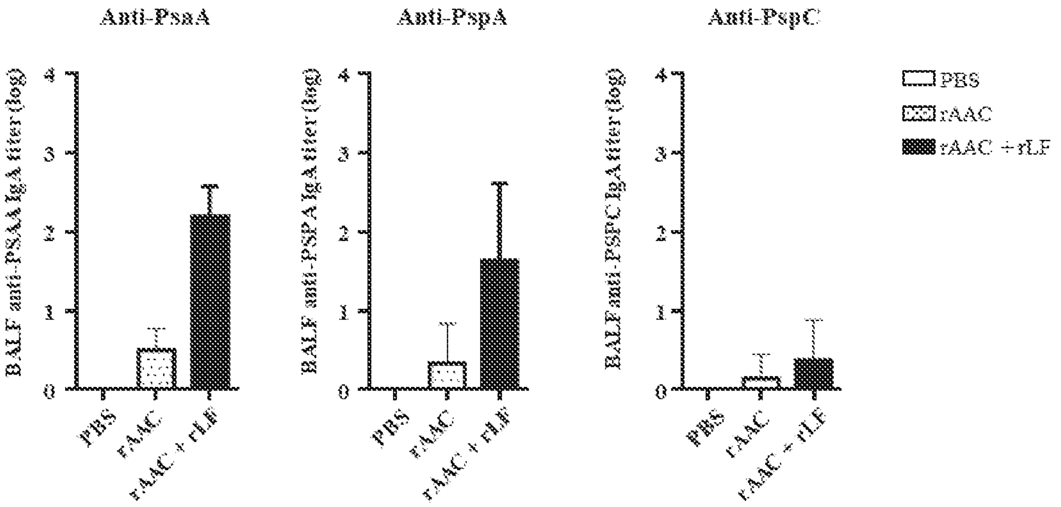

As showed in FIG. 9 and FIGS. 10A-10B, the lipidated FLIPr strongly enhances rAAC-induced systemic and mucosal antibody responses.

Cytokine Production Profiles Induced by rAAC Adjuvanted with rLF.

Groups of mice are vaccinated twice with PBS, rAAC, or rAAC adjuvanted with rLF (rAAC+rLF). PBS-immunized mice are alone served as control. Splenocytes are cultured and stimulated with rAAC for 4 days. Stimulation with BSA or medium alone served as controls. The supernatants are collected to evaluate levels of Th1-type cytokines (IFN-γ), Th2-type cytokines (IL-13), and Th17-type cytokines (IL-17A) by ELISA.

Figure 11:
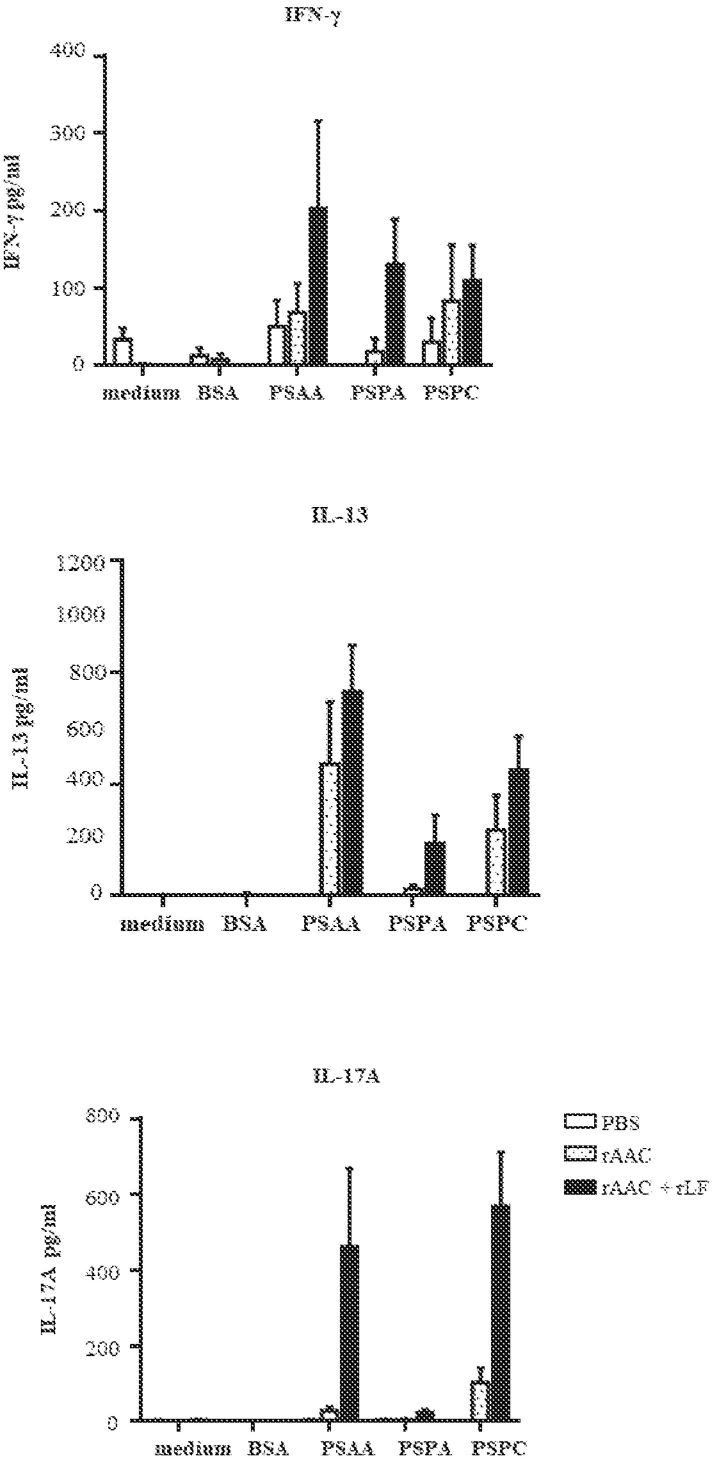
FIG. 11 shows the cytokine production profiles induced by rAAC adjuvanted with rLF.

As showed in FIG. 11, the lipidated FLIPr-adjuvanted of pneumococcal vaccine is able to stimulate rAAC-specific broad-spectrum T cell responses.

The Protective Effect Against *S. pneumoniae* Induced by rAAC Adjuvanted with rLF Groups of mice intranasally immunized three times with PBS, rAAC or rAAC adjuvanted with rLF (rAAC+rLF). The percent survival of mice after challenge by intranasal inoculation with $2\times10^5$ CFU of the *S. pneumoniae* D39 strain.

Figure 12:
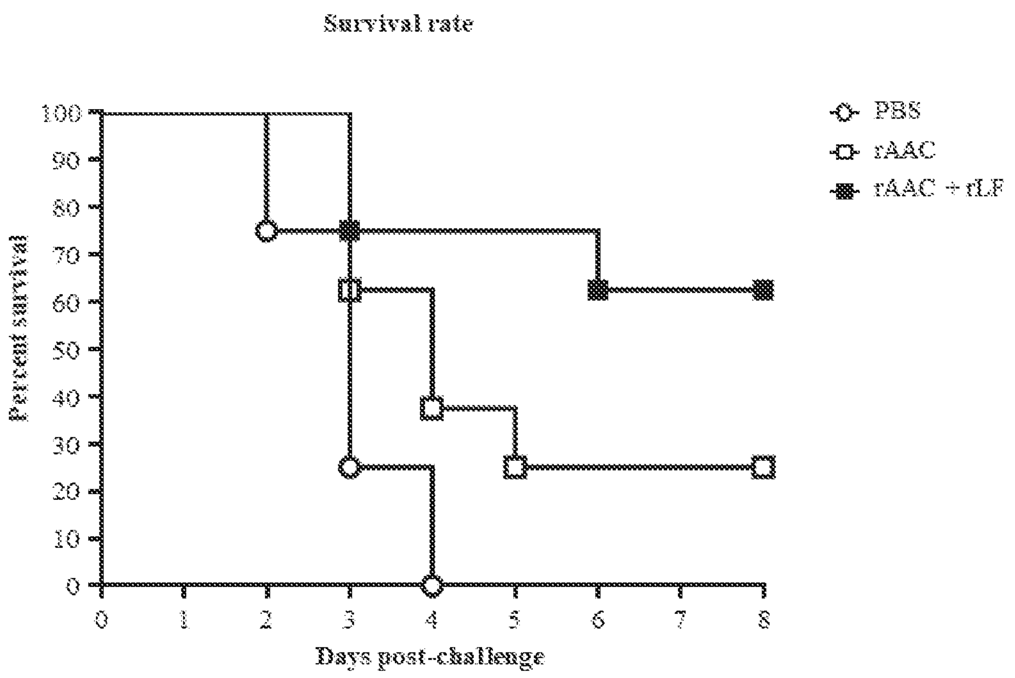
FIG. 12 shows the protective effect against *S. pneumoniae* induced by rAAC adjuvanted with rLF.

As showed in FIG. 12, the lipidated FLIPr increased rAAC-induced protection effect against *S. pneumoniae* challenge.

Antibody Responses Induced by Intranasal Immunization of Inactived Zika Virus (IZV) Adjuvanted with Recombinant Lipidated FLIPr (rLF)

Groups of mice intranasally immunized twice with PBS, IZV, or IZV adjuvanted with rLF (IZV+rLF). The titers of anti-IZV IgG antibodies in the serum are determined by ELISA. The titers of anti-rZE3 IgG antibodies in the serum are determined by ELISA.

Figure 13A:
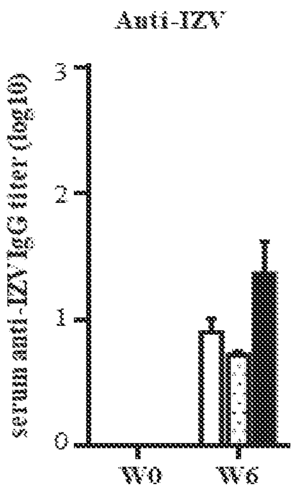
FIGS. 13A-13B show the antibody responses induced by intranasal immunization of inactived Zika virus (IZV) adjuvanted with recombinant lipidated FLIPr (rLF). The titers of anti-IZV IgG (A) and anti-rZE3 IgG (B) antibodies in the serum were determined by ELISA.
Figure 13B:
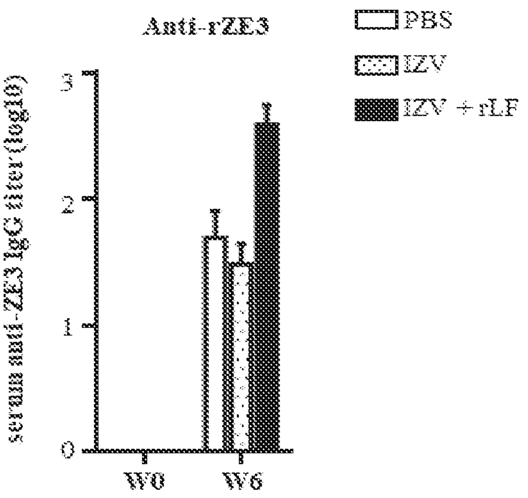

As showed in FIGS. 13A-13B, the lipidated FLIPr also enhanced antibody responses induced by inactivated Zika virus.

Antibody Responses Induced by Intranasal Immunization of Inactive Influenza Viruses H7N9 (IH7N9) Adjuvanted with Recombinant Lipidated FLIPr (rLF)

Groups of mice are vaccinated twice with IH7N9, or IH7N9 adjuvanted with rLF (IH7N9+rLF). The titers of anti-IH7N9 IgG antibodies in the serum are determined by ELISA. The titers of anti-IH7N9 IgA antibodies in mucosal tissue are determined by ELISA, including nasal wash and bronchoalveolar lavage fluid (BALF).

Figure 14A:
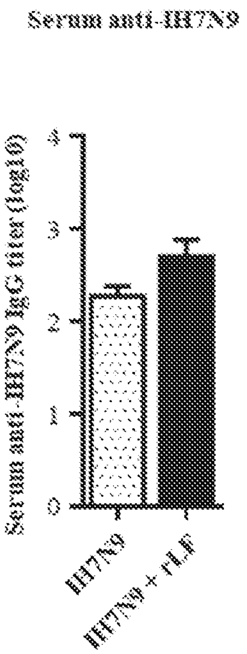
FIGS. 14A-14C show the antibody responses induced by intranasal immunization of inactive influenza viruses H7N9 (IH7N9) adjuvanted with recombinant lipidated FLIPr (rLF). (A) The titers of anti-IH7N9 IgG antibodies in the serum were determined by ELISA. The titers of anti-IH7N9 IgA antibodies in mucosal tissue were determined by ELISA, including (B) nasal wash and (C) bronchoalveolar lavage fluid (BALF).
Figure 14B:
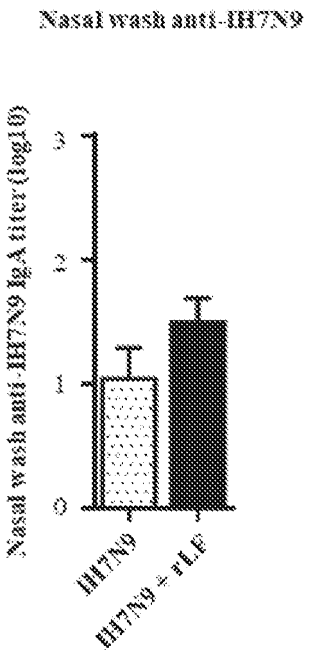
Figure 14C:
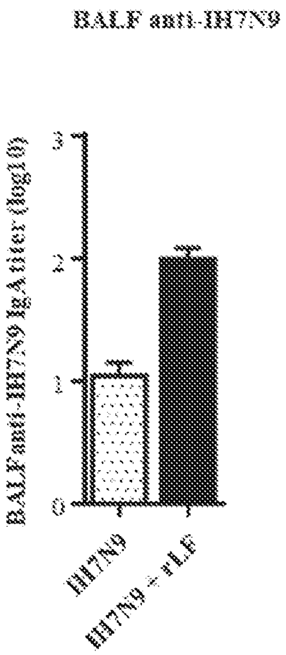

As showed in FIGS. 14A-14C, the lipidated FLIPr enhanced systemic and mucosal antibody responses induced by inactivated influenza virus.

As the results, the lipidated FLIPr can be widely used in vaccines with different antigens, including recombinant proteins and inactivated virus vaccines to enhance specific antibody and T-cell immune responses.

While the present disclosure has been described in conjunction with the specific embodiments set forth above, many alternatives thereto and modifications and variations thereof will be apparent to those of ordinary skill in the art. All such alternatives, modifications and variations are regarded as falling within the scope of the present disclosure.

What is claimed is:

1. A vaccine composition, comprising a recombinant lipidated FLIPr (rLF) and an immunogen, wherein the recombinant lipidated FLIPr (rLF) and the immunogen are present as separate molecular entities, and wherein the recombinant lipidated FLIPr (rLF) is used to enhance a vaccine immune response of the immunogen.

2. The vaccine composition according to claim 1, wherein the recombinant lipidated FLIPr (rLF) comprises a lipidating sequence and a polypeptide of FLIPr.

3. The vaccine composition according to claim 1, wherein the recombinant lipidated FLIPr (rLF) is used to induce anti-FLIPr responses.

4. The vaccine composition according to claim 1, wherein the recombinant lipidated FLIPr (rLF) is used to prevent phagocytosis inhibition caused by *S. aureus* FLIPr protein.

5. The vaccine composition according to claim 1, wherein the immunogen is a subunit protein of a virus or a bacterium.

6. The vaccine composition according to claim 5, wherein the immunogen is a recombinant envelope protein domain III of Zika virus (rZE3).

7. The vaccine composition according to claim 5, wherein the immunogen is a recombinant mixture of the *S. pneumoniae* pneumococcal proteins (rAAC) comprising pneumococcal surface adhesin A (rPsaA), pneumococcal surface protein A (rPspA), and pneumococcal surface protein C (rPspC).

8. The vaccine composition according to claim 5, wherein the immunogen is a recombinant trimeric spike protein of SARS COV-2 (ITS).

9. The vaccine composition according to claim 1, wherein the immunogen is an inactivated virus.

10. The vaccine composition according to claim 9, wherein the immunogen is an inactivated Zika virus (IZV).

11. The vaccine composition according to claim 9, wherein the immunogen is an inactivated influenza virus.

* * * * *